US00PP32216P3

(12) United States Plant Patent
Bell et al.

(10) Patent No.: US PP32,216 P3
(45) Date of Patent: Sep. 22, 2020

(54) BLUEBERRY PLANT NAMED 'MG11543-23-004'

(50) Latin Name: ***Vaccinium* hybrid**
Varietal Denomination: MG11543-23-004

(71) Applicant: Moondarra Genetics Pty Ltd, Moondarra, Victoria (AU)

(72) Inventors: Ridley Bell, Lindendale (AU); Joel Deveson, Newborough (AU)

(73) Assignee: Moondarra Genetics PTY LTD, Moondarra (AU)

( * ) Notice: Subject to any disclaimer, the term of this patent is extended or adjusted under 35 U.S.C. 154(b) by 0 days.

(21) Appl. No.: 16/501,663

(22) Filed: May 20, 2019

(65) Prior Publication Data

US 2019/0364711 P1 Nov. 28, 2019

Related U.S. Application Data

(60) Provisional application No. 62/762,835, filed on May 22, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Plant & Planet Law Firm

(57) ABSTRACT

The new blueberry plant variety 'MG11543-23-004' is provided. 'MG11543-23-004' is a commercial variety intended for the fresh fruit market. The variety is produced from a cross of 'Brigitta' (seed parent, not patented) and 'Ridley 1403' (pollen parent, U.S. Plant Pat. No. 25,432), which can be distinguished by its outstanding features.

3 Drawing Sheets

Latin name of the genus and species:
Genus—*Vaccinium.*
Species—hybrid.

VARIETY DENOMINATION

The new blueberry plant claimed is of the variety denominated 'MG11543-23-004'.

BACKGROUND OF THE INVENTION

The proposed new variety of the denomination 'MG11543-23-004' was selected as a seedling from a controlled pollination involving northern and southern highbush varieties 'Brigitta' (seed parent) (not patented) and 'Ridley 1403' (pollen parent) (U.S. Plant Pat. No. 25,432) respectively. The cross was made in 2011 in Moondarra, Victoria, Australia and the variety was selected in 2015 in Moondarra, Victoria, Australia. The plants of 'MG11543-23-004' are strong and vigorous with an upright to whippy growth habit. The fruit is medium to large, with a crunchy texture and a moderate bloom and good flavour.

This new cultivar has been asexually propagated through softwood cuttings since 2016 and grown in replicated field trials from 2017 in Moondarra, Victoria, Australia.

SUMMARY OF THE INVENTION

The proposed new *Vaccinium* hybrid cultivar 'MG11543-23-004' was a selection resulting from a cross between northern and southern highbush varieties 'Brigitta' (seed parent) (not patented) and 'Ridley 1403' (pollen parent) (U.S. Plant Pat. No. 25,432) respectively.

The seed parent 'Brigitta' was produced from open pollinated 'Lateblue' (not patented) seeds sent to the Knoxfield Horticultural Research Institute in Victoria, Australia in 1976, and was selected based on its vigorous growth, medium sized berry, mid-season fruit ripening and medium to firm fruit firmness.

The pollen parent 'Ridley 1403' was produced from a southern highbush seedling selection of 'S02-25-05' (unpatented) and pollen parent 'S03-08-02' (unpatented) and was selected in 2008 at Lindendale, New South Wales, Australia with the criteria of strong plant vigor, early-mid fruit ripening, very large fruit size and very firm/crunchy fruit texture.

The proposed new *Vaccinium* hybrid cultivar 'MG11543-23-004' was the product of a controlled cross pollination between northern highbush variety 'Brigitta' and southern highbush variety 'Ridley 1403' in the breeding program at Moondarra, Victoria, Australia in 2011.

Asexual reproduction of the proposed new variety 'MG11543-23-004' by cutting propagation has occurred since 2016 at Moondarra, Victoria, Australia. This has demonstrated that the new variety is uniform, stable and true to type over successive generations of asexual propagation in respect to the aforementioned characteristics.

The proposed new *Vaccinium* hybrid cultivar 'MG11543-23-004' was a single plant selection from a population of seedlings grown from a cross between northern highbush variety 'Brigitta' and southern highbush variety 'Ridley 1403' in the controlled breeding program at Moondarra, Victoria, Australia, selected in 2015. The selection of 'MG11543-23-004' was based upon strong plant vigor, very crunchy fruit with good flavor and a medium to large berry size. 'MG11543-23-004' was under the breeder code NB-23-4 during field trial evaluations from 2017.

The following characteristics of the proposed new variety have been observed and used to distinguish 'MG11543-23-004' as a distinct cultivar of *Vaccinium* hybrid:

Upright/whippy growth habit.
Mid-season timing of fruit ripening.
Strong plant vigor.
Medium to large berry size.
Small, dry picking scar
Crunchy berry texture.
Low to moderate sweetness.
Moderate bloom.

The proposed new variety 'MG11543-23-004' is uniform, stable and true to type over successive generations of asexual propagation through softwood cuttings in respect to the characteristics aforementioned.

The new cultivar 'MG11543-23-004' differs from the pollen parent 'Ridley 1403' in exhibiting an expected higher tolerance to cold, smaller berry size, later flowering and a higher acid flavor.

'MG11543-23-004' differs from the seed parent 'Brigitta' in respect to a larger berry size, stronger bloom, an expected lower tolerance to cold climates and a crunchier berry texture.

BRIEF DESCRIPTION OF THE DRAWINGS

The accompanying photographic illustration shows typical specimens in full color of the foliage and fruit of the new variety 'MG11543-23-004'. 'MG11543-23-004' has been labeled KALINDA NB23-4 in the photographs. The colors are as nearly true as is reasonably possible in a color representation of this type. The colors in the photographs are as close as possible with the photographic and printing technology utilized. The color values cited in the detailed botanical description accurately describe the colors of the new blueberry.

DETAILED BOTANICAL DESCRIPTION

Figure 1:
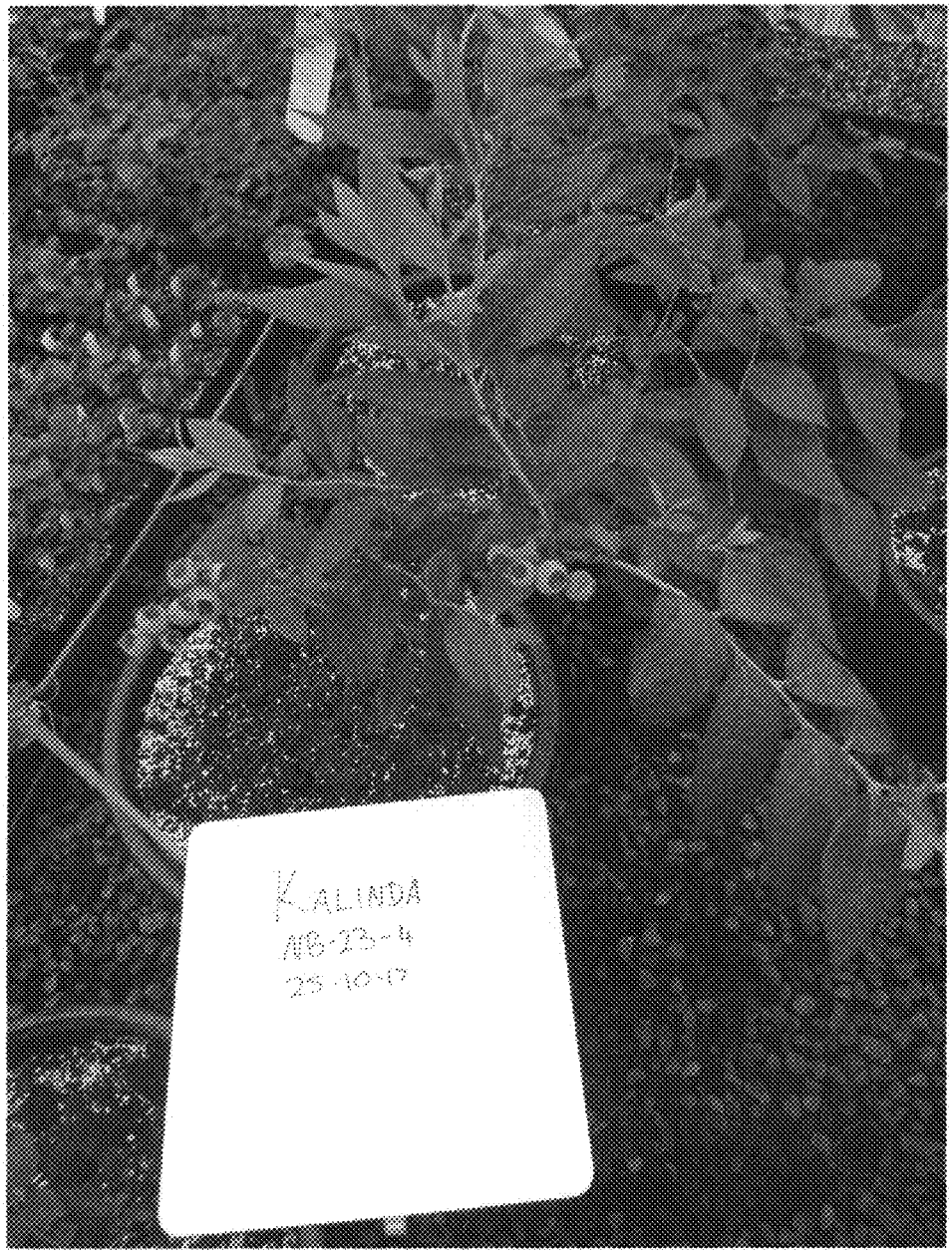
FIG. 1 is a photograph of the new variety 'MG11543-23-004', demonstrating the plant's compact growth habit at approximately 1 year of age.
Figure 2:
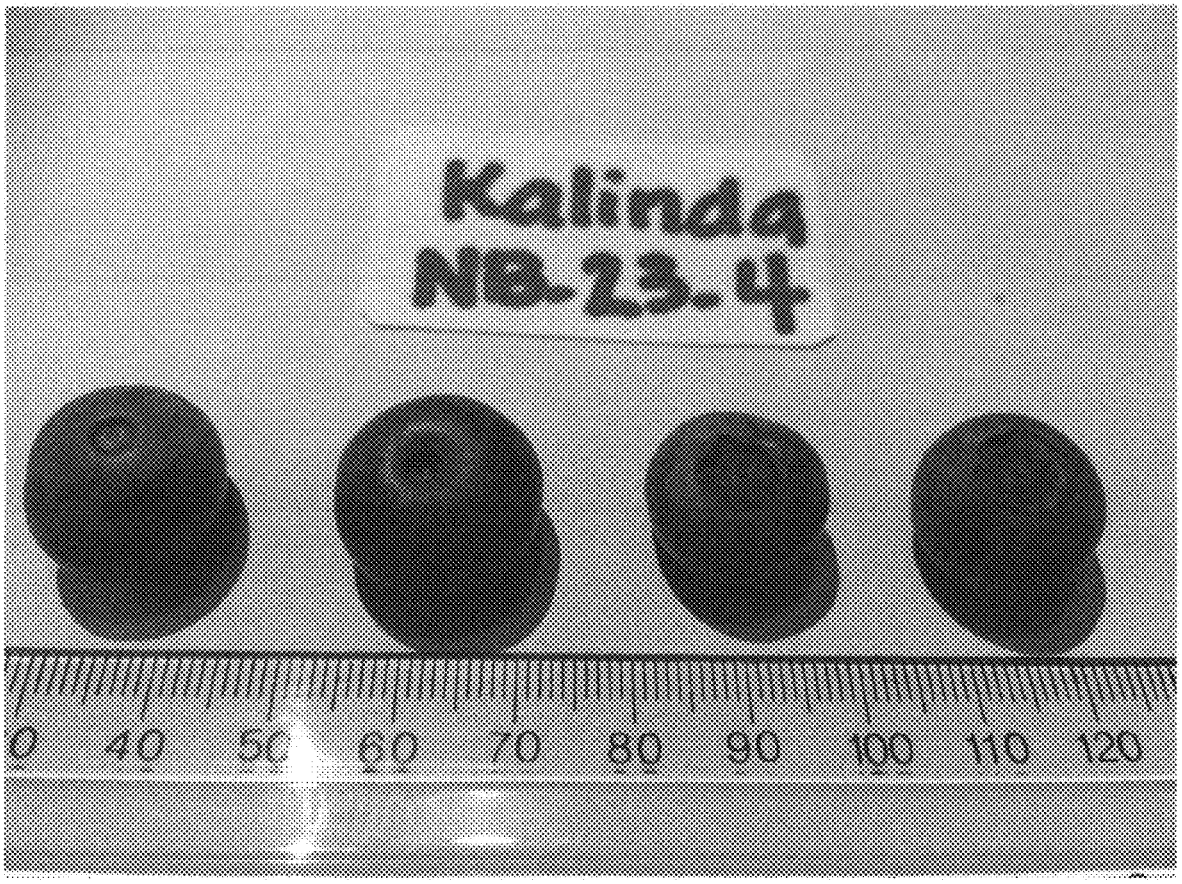
FIG. 2 is a photograph of the new variety 'MG11543-23-004', demonstrating the plant's fruit at approximately 1 year of age.
Figure 3:
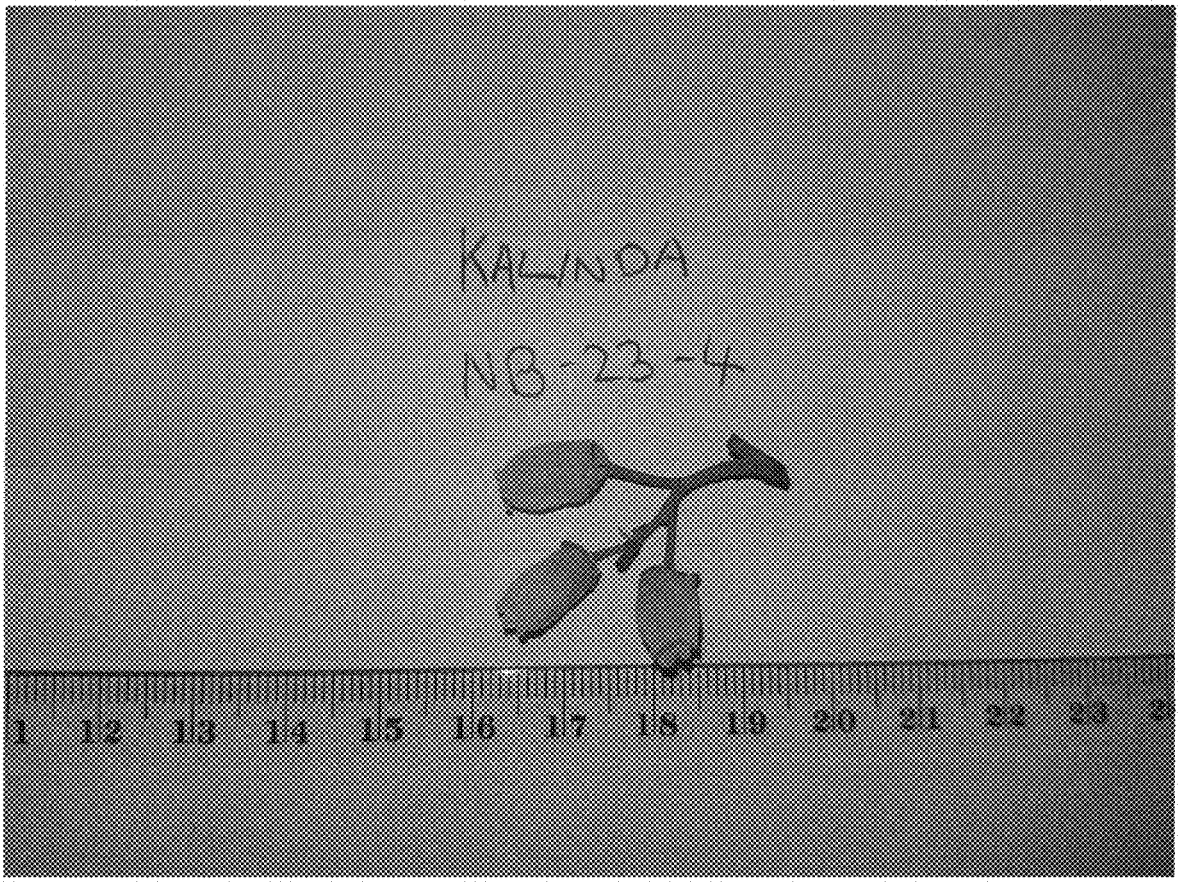
FIG. 3 is a photograph of the new variety 'MG11543-23-004', demonstrating the plant's flowers at approximately 1 year of age.

The following detailed description sets forth the distinctive characteristics of 'MG11543-23-004'. The data which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Moondarra, Victoria, Australia. Descriptions of fruit characteristics were made on fruit grown in Moondarra, Victoria, Australia. Color designations are from Pantone Colour Bridge Plus.

Classification:

a. *Family*.—Ericaceae.
b. *Genus*.—*Vaccinium*.
c. *Species*.—Hybrid.
d. *Common name*.—Blueberry.

Parentage:

*Female parent*.—'Brigitta.' (not patented).
*Male parent*.—'Ridley 1403' (U.S. Pat. No. 25,432).

Market class: A fruiting plant intended for the fresh fruit market.

PLANT

General:

a. *Parentage*.—'Brigitta' x 'Ridley1403'.
b. *Plant height*.—~1.1 m.
c. *Plant width*.—0.5-0.6 m.
d. *Growth habit*.—Upright/whippy.
e. *Growth*.—Medium to strong vigor.
f. *Productivity*.—Medium to high (~7.6 kg/plant).
g. *Cold hardiness*.—Not tested.
h. *Cold tolerance*.—Not tested.
i. *Chilling requirement*.—Not tested.
j. *Tolerance to disease*.—Not tested.
k. *Leafing*.—Moderate-strong.
l. *Twigginess*.—Low-moderate.

STEM

General:

a. *Suckering tendency*.—4-6 no. canes per plant.
b. *Mature cane color*.—197C/164B-165D.
c. *Mature cane length*.—0.6-0.75 m.
d. *Mature cane width*.—9 cm.
e. *Bark texture*.—Medium roughness.
f. *Surface texture of new wood*.—Smooth.
g. *Internode length on strong, new shoots*.—20-26 mm.
h. *Fruiting wood*.—To 17 cm in length.

FOLIAGE

General:

a. *Time of beginning of leaf bud burst*.—Early ($12^{th}$) September.
b. *Leaf color* (*top side*).—135B/137A.
c. *Leaf color* (*under side*).—146C/145B.
d. *Leaf arrangement*.—Alternate.
e. *Leaf shape*.—Elliptic.
f. *Leaf margins*.—Entire.
g. *Undulation of margin*.—Weak.
h. *Leaf venation*.—Reticulate.
i. *Leaf apices*.—Acute.
j. *Leaf bases*.—Obtuse.
k. *Leaf length*.—65-70 mm.
l. *Leaf width*.—33-35 mm.
m. *Leaf length/width ratio*.—Medium; 1:0.51-1:0.5.
n. *Leaf nectarines*.—Absent.
o. *Pubescence of upper side*.—Absent.
p. *Pubescence of lower side*.—Absent.
q. *Cross sectional profile*.—Flat.
r. *Longitudinal profile*.—Straight.
s. *Attitude*.—Semi-upright.

Petioles:
a. *Length.*—~4 mm.
b. *Width.*—1-2 mm.
c. *Color.*—Yellow-Green 144C/145A.

FLOWERS

General:
a. *Time of beginning of flowering.*—15th September.
b. *Time of* 50% *anthesis.*—Late September/early October.
c. *Flower shape.*—Urceolate.
d. *Flower bud density.*—Low to moderate.
e. *Flower fragrance.*—Weak; sweet smell.

Corolla:
*Length.*—11-12 mm.
*Width.*—6-7 mm.
*Aperture width.*—~4 mm.
*Anthocyanin coloration of corolla.*—Absent.
*Corolla ridges.*—Present.
*Protrusion of stigma.*—Absent.

Inflorescence:
a. *Length.*—25-33 mm.
b. *Diameter.*—20-24 mm.
c. *Length of peduncle.*—7-8 mm.
d. *Surface texture of peduncle.*—Smooth.
e. *Color of peduncle.*—146C.
f. *Length of pedicel.*—~6 mm.
g. *Surface texture of pedicel.*—Smooth.
h. *Color of pedicel.*—370CP.
i. *Number of flowers per cluster.*—4-5.
j. *Flower cluster density.*—Light to moderate.

Calyx (with sepals):
a. *Diameter.*—7-8 mm.
b. *Color* (*sepals*).—140B/143C.

Stamen:
a. *Length.*—8-9 mm.
b. *Number per flower.*—9-10.
c. *Filament color.*—142C.
d. *Style length.*—~7 mm.
e. *Color.*—145B.

Style:
a. *Length.*—~7 mm.
b. *Color.*—145B.

Pistil:
a. *Length.*—~9 mm.
b. *Ovary color* (*exterior*).—137A/146A.

Anther:
a. *Length.*—~4 mm.
b. *Number.*—9-10.
c. *Color.*—164A/N163C.

Pollen:
*Self-compatibility.*—Yes.

FRUIT

General:
a. *Time of fruit ripening.*—Mid; December to January in Moondarra, Victoria, Australia.
b. *Time of* 50% *maturity.*—Mid November.
c. *Fruit development period.*—Approximately 70 days.
d. *Cluster density.*—~23 berries per cluster.
e. *Unripe fruit color.*—140B.
f. *Ripe berry color.*—203C.
g. *Berry surface wax abundance.*—Strong.
h. *Berry flesh color.*—145C/D.
i. *Berry weight.*—3.2 g.
j. *Berry height from calyx to scar.*—11-12 mm.
k. *Berry diameter.*—16-17 mm.
l. *Berry shape.*—Oblate.
m. *Fruit stem scar.*—Small/dry.
n. *Sweetness when ripe.*—Low-medium.
o. *Firmness when ripe.*—Firm.
p. *Acidity when ripe.*—Medium.
q. *Storage quality.*—Good.
r. *Self-fruitfulness.*—Yes.
s. *Uses.*—Fresh fruit.

SEED

General:
a. *Seed abundance in fruit.*—Low-medium.
b. *Seed length.*—~1 mm.

COMPARISON BETWEEN PARENTAL AND COMMERCIAL CULTIVARS

| Organ | Context | 'MG11543-23-004' | 'Ridley 1403' (U.S. Plant Pat. No. 25,432) |
|---|---|---|---|
| Plant | Vigour | Medium to strong | Strong |
| Plant | Growth habit | Upright | Upright to semi-upright |
| One-year-old shoot | Color | Green | Green |
| One-year-old shoot | Length of internode | Short to medium; 20-26 mm | Medium |
| Leaf | Length | Long; 65-70 mm | Long to very long |
| Leaf | Width | Medium to broad; 33-25 mm | Broad |
| Leaf | Shape | Elliptic | Elliptic |
| Leaf | Color of upper side | Green; 135B/137A | Green |
| Leaf | Intensity of green color on upper side (varieties with green leaf colour only) | Dark | Medium |
| Leaf | Margin | Entire | Entire |
| Flower bud | Anthocyanin coloration | Weak to medium | Weak |
| Flower | Shape of corolla | Urceolate | Urceolate |
| Flower | Size of corolla tube | Medium | Medium to large |
| Flower | Anthocyanin coloration of corolla tube | Absent or very weak | Absent or very weak |
| Flower | Ridges on corolla tube | Present | Present |
| Fruit cluster | Density | Sparse to medium | Medium to dense |
| Unripe fruit | Intensity of green color | Medium | Light |
| Fruit | Size | Medium to large; 16-17 mm | Very large |
| Fruit | Shape in longitudinal section | Oblate | Round |
| Fruit | Attitude of sepals | Erect to semi-erect | Erect |
| Fruit | Diameter of calyx basin | Medium | Large |
| Fruit | Depth of calyx basin | Shallow | Deep |
| Fruit | Intensity of bloom | Strong | Medium |
| Fruit | Color of skin | Dark blue; 203C | Dark blue |
| Fruit | Firmness | Firm | Very firm |
| Fruit | Sweetness | Medium | High |
| Fruit | Acidity | Low | Low |

-continued

COMPARISON BETWEEN PARENTAL AND COMMERCIAL CULTIVARS

| | | | |
|---|---|---|---|
| Time of | Vegetative bud burst | Early to medium | Early |
| Time of | Beginning of flowering | Early to medium | Early |
| Time of | Beginning of fruit ripening | Medium | Early |

| Organ | Context | 'Ridley 1812 (not patented) |
|---|---|---|
| Plant | Vigour | Medium |
| Plant | Growth habit | Upright |
| One-year-old shoot | Color | Green |
| One-year-old shoot | Length of internode | Medium |
| Leaf | Length | Long to very long |
| Leaf | Width | Broad |
| Leaf | Shape | Elliptic |
| Leaf | Color of upper side | Green |
| Leaf | Intensity of green color on upper side (varieties with green leaf colour only) | Medium |
| Leaf | Margin | Entire |
| Flower bud | Anthocyanin coloration | Weak |
| Flower | Shape of corolla | Urceolate |
| Flower | Size of corolla tube | Medium |

-continued

COMPARISON BETWEEN PARENTAL AND COMMERCIAL CULTIVARS

| | | |
|---|---|---|
| Flower | Anthocyanin coloration of corolla tube | Absent or very weak |
| Flower | Ridges on corolla tube | Present |
| Fruit cluster | Density | Medium |
| Unripe fruit | Intensity of green color | Light |
| Fruit | Size | Very large |
| Fruit | Shape in longitudinal section | Oblate |
| Fruit | Attitude of sepals | Erect |
| Fruit | Diameter of calyx basin | Large to very large |
| Fruit | Depth of calyx basin | Deep to very deep |
| Fruit | Intensity of bloom | Medium |
| Fruit | Color of skin | Dark blue |
| Fruit | Firmness | Medium |
| Fruit | Sweetness | Medium to high |
| Fruit | Acidity | Medium to high |
| Time of | Vegetative bud burst | Medium |
| Time of | Beginning of flowering | Early |
| Time of | Beginning of fruit ripening | Early-medium |

The invention claimed is:

1. A new and distinct variety of blueberry plant named 'MG11543-23-004', substantially as illustrated and described herein.

* * * * *